US009872816B2

(12) United States Patent
Boswell et al.

(10) Patent No.: US 9,872,816 B2
(45) Date of Patent: Jan. 23, 2018

(54) BARRIER PATCH OF A FOAMED FILM AND METHODS OF IMPROVING SKIN APPEARANCE

(71) Applicant: The Procter & Gamble Company, Cincinnati, OH (US)

(72) Inventors: Emily Charlotte Boswell, Cincinnati, OH (US); Elizabeth Anne Wilder, West Chester, OH (US); Michael Remus, Heidelberg (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/296,736

(22) Filed: Oct. 18, 2016

(65) Prior Publication Data

US 2017/0112726 A1    Apr. 27, 2017

Related U.S. Application Data

(60) Provisional application No. 62/245,040, filed on Oct. 22, 2015, provisional application No. 62/257,351, filed on Nov. 19, 2015.

(51) Int. Cl.
| | |
|---|---|
| A61K 8/02 | (2006.01) |
| A61K 8/81 | (2006.01) |
| A61K 8/06 | (2006.01) |
| A61K 8/04 | (2006.01) |
| A61K 8/67 | (2006.01) |
| A61K 8/34 | (2006.01) |
| A61Q 19/00 | (2006.01) |
| A45D 44/00 | (2006.01) |

(52) U.S. Cl.
CPC .......... *A61K 8/0208* (2013.01); *A45D 44/002* (2013.01); *A61K 8/046* (2013.01); *A61K 8/062* (2013.01); *A61K 8/345* (2013.01); *A61K 8/671* (2013.01); *A61K 8/673* (2013.01); *A61K 8/675* (2013.01); *A61K 8/678* (2013.01); *A61K 8/8111* (2013.01); *A61K 8/8135* (2013.01); *A61Q 19/00* (2013.01); *A61K 2800/10* (2013.01); *A61K 2800/30* (2013.01); *A61K 2800/412* (2013.01); *A61K 2800/54* (2013.01); *A61K 2800/87* (2013.01); *A61K 2800/884* (2013.01)

(58) Field of Classification Search
CPC .............................. A61K 8/028; A61K 8/8111
See application file for complete search history.

(56) References Cited

U.S. PATENT DOCUMENTS

| | | | |
|---|---|---|---|
| 4,341,209 A | 7/1982 | Schaar | |
| 4,377,616 A | 3/1983 | Ashcraft et al. | |
| 4,472,328 A | 9/1984 | Sugimoto et al. | |
| 4,578,297 A | 3/1986 | Duncan | |
| 4,649,186 A * | 3/1987 | Jenkins ................. | C08F 210/02 526/218.1 |
| 4,773,408 A | 9/1988 | Cilento et al. | |
| 4,781,294 A | 11/1988 | Croce | |
| 5,180,626 A | 1/1993 | Ishibashi et al. | |
| 5,455,043 A | 10/1995 | Fischel-Ghodsian | |
| 5,476,664 A | 12/1995 | Robinson et al. | |
| 5,503,844 A * | 4/1996 | Kwiatek ............... | A61K 9/7084 424/434 |
| 5,629,014 A | 5/1997 | Kwiatek et al. | |
| 6,162,458 A | 12/2000 | Asada et al. | |
| 6,277,401 B1 * | 8/2001 | Bello ................... | A61K 9/7084 424/443 |
| 6,495,229 B1 | 12/2002 | Carte et al. | |
| 6,593,602 B2 | 7/2003 | Liang et al. | |
| 6,676,962 B1 | 1/2004 | Muller | |
| 7,063,859 B1 * | 6/2006 | Kanios ................. | A61K 9/7053 424/448 |
| 8,173,233 B2 | 5/2012 | Rogers et al. | |
| 8,512,837 B2 | 8/2013 | Dow | |
| 2003/0152610 A1 | 8/2003 | Rolf et al. | |
| 2003/0167556 A1 | 9/2003 | Kelley | |
| 2004/0116018 A1 | 6/2004 | Clark | |
| 2005/0266059 A1 | 12/2005 | Poss | |
| 2006/0121097 A1 | 6/2006 | Lodge et al. | |
| 2006/0198879 A1 * | 9/2006 | Fukuta ................. | A61K 9/7084 424/448 |
| 2007/0292491 A1 | 12/2007 | Hansen et al. | |
| 2007/0298089 A1 | 12/2007 | Saeki et al. | |

(Continued)

FOREIGN PATENT DOCUMENTS

| | | |
|---|---|---|
| EP | 0904049 | 3/1999 |
| JP | 2011-178693 | 9/2011 |
| WO | WO 97/32567 | 9/1997 |
| WO | WO00/30694 | 6/2000 |
| WO | WO03/063817 | 8/2003 |
| WO | WO 03/084579 | 10/2003 |

OTHER PUBLICATIONS

PCT International Search Report, dated Dec. 23, 2016, 12 pages.
Foamed Films Find New Niches: Plastic Technology, by Jan Schut, Jan. 2002 Issue, 5 pages.

*Primary Examiner* — Kyle Purdy

(74) *Attorney, Agent, or Firm* — Betty J. Zea

(57) ABSTRACT

A beauty care product is provided. The beauty care product has a multi-layered barrier patch with a non-foamed first layer and a foamed second layer. The non-foamed first layer has a non-foamed polymer film with a first surface and a thickness from 5 microns to 250 microns. The foamed second layer has a foamed polymer film comprising a Mean Void Volume Percentage from 45% to 80% and a thickness of from 10 microns to 250 microns. The beauty care product also has a cosmetic composition with an effective amount of a skin active agent and a pressure sensitive adhesive.

28 Claims, 2 Drawing Sheets

(56) References Cited

U.S. PATENT DOCUMENTS

| | | |
|---|---|---|
| 2008/0138593 A1 | 6/2008 | Martinez |
| 2009/0155326 A1 | 6/2009 | Mack et al. |
| 2009/0317578 A1 | 12/2009 | Rogers et al. |
| 2009/0317605 A1 | 12/2009 | Rogers et al. |
| 2011/0200652 A1 | 8/2011 | Smith |
| 2013/0042417 A1 | 2/2013 | Smith |
| 2013/0178407 A1 | 7/2013 | Henkel |
| 2014/0079938 A1 | 3/2014 | Perick et al. |
| 2014/0083878 A1* | 3/2014 | Tang .................. A61K 9/7069 206/204 |
| 2014/0376835 A1 | 12/2014 | Roger et al. |
| 2014/0377512 A1 | 12/2014 | Rogers et al. |
| 2015/0307264 A1 | 10/2015 | Boswell et al. |

\* cited by examiner

BARRIER PATCH OF A FOAMED FILM AND METHODS OF IMPROVING SKIN APPEARANCE

TECHNICAL FIELD

The present invention relates to products comprising foamed film suitable for improving skin appearance. The present invention also relates to a method of delivering cosmetic compositions to a target area of the skin via the use of a barrier patch made from the foamed film.

BACKGROUND OF THE INVENTION

The benefits of using a patch or mask device comprising skin agents to treat the skin, have been recognized in the art. Some cosmetic patches or devices are commercially marketed or described as being useful for the delivery of skin care actives such as vitamins, anti-acne actives, moisturizers and the like. Patches have also been described in the literature and marketed in the medical field as a useful means for the transdermal administration of drugs.

However, many patches or devices suffer drawbacks in their physical product forms resulting in undesirable in-use characteristics as perceived by the wearer. These drawbacks include patches that do not provide occlusion of the skin treatment area, patches that look heavy, opaque and non breathable, signaling a less comfortable in use experience for the consumer, or patches that do not actually deliver an effective amount of the active ingredient to the skin.

In particular some patches are opaque, dry, rough, thick, and/or highly impermeable to air, fluids and moisture. These patches may be tight, stiff, hot, heavy, inflexible, and uncomfortable to wear. Even before wearing the patch, consumers may have the impression on seeing the patch, it will be uncomfortable to wear. This first impression is especially important when the recommended wear time is for an extended period such as overnight.

Film materials which are impermeable to liquid but permeable to vapor are known as breathable and have been described in the art. Woven materials such as silk, satin and soft, thick cotton fabrics, are also known and are usually both vapor and liquid permeable. Breathable, permeable materials may provide a comfortable wearing experience. However, highly breathable materials will permit some self-drying of a patch containing actives or liquid compositions. This drying out of the product may have several disadvantages. Drying out of the actives may negate the benefits of occluding the skin. In addition any incompatibility between the skin agents and the adhesive materials used with a patch, may be exacerbated by the drying of the patch. This may lead to ineffective partitioning of the skin agents through the adhesive layer to the skin.

It is advantageous to have a thin and flexible patch that conforms and fits the contours of the face or other target skin area. Thin films, however, worn on the face may be predisposed to wrinkling in use. If the patch is made stiffer or the thickness is increased, the patch may feel more heavy and tight to the consumer during wear.

It has now been found that a user's satisfaction may be improved by rebalancing certain properties of the patch product. By selecting and creating the proper degree foaming in the films used and by providing foamed layer(s) with non-foamed layer(s), the patch appears more breathable and high quality through the proper degree of light reflection and optical effects. The multilayered barrier patch is also flexible and provides low permeability and high occlusion so that skin active agents are effectively delivered to the skin. A positive consumer experience is provided since the product looks luxurious and breathable and feels lightweight and flexible to the consumer.

SUMMARY OF THE INVENTION

The present invention solves at least one of these problems by incorporating at least one foamed film layer into a beauty care product and is directed, in part, to having the correct degree of foaming.

In one aspect thus a beauty care product is provided comprising:
a multi-layered barrier patch comprising:
  (i) a non-foamed first layer comprising a non-foamed polymer film having a first surface, and having a thickness from about 5 microns to about 250 microns, preferably from 10 microns to 40 microns; and preferably the first layer comprises ethylene vinyl acetate;
  (ii) a foamed second layer comprising a foamed polymer film comprising a Mean Void Volume Percentage from about 45% to about 80%, preferably from about 50% to about 75%, more preferably from about 55% to about 73%, and a thickness of from about 10 microns to about 250 microns, preferably from about 40 microns to about 160 microns; and preferably the second layer comprises ethylene vinyl acetate;
  wherein the barrier patch comprises a Flop Index (FI) from about 2.5 to about 15 according to ASTM E2539, preferable the FI is from about 2.5 to about 6 or from about 3 to about 6; and
a cosmetic composition comprising an effective amount of a skin active agent; and
a pressure sensitive adhesive.

In another aspect a beauty care product is provided comprising:
a multi-layered barrier patch comprising:
  (i) a non-foamed first layer comprising a non-foamed polymer film having a first surface, and having a thickness from about 5 microns to about 250 microns, preferably from 10 microns to 40 microns; and preferably the first layer comprises ethylene vinyl acetate;
  (ii) a foamed second layer comprising a foamed polymer film comprising a Mean Void Volume Percentage from about 45% to about 80%, preferably from about 50% to about 75%, more preferably from about 55% to about 73%, and a thickness of from about 10 microns to about 250 microns, preferably from about 40 microns to about 160 microns; and preferably the second layer comprises ethylene vinyl acetate;
  wherein the barrier patch comprises a flexibility from about 0.009 gfcm$^2$/cm to about 0.14 gfcm$^2$/cm, preferably from about 0.01 gfcm$^2$/cm to about 0.055 gfcm$^2$/cm, more preferably from about 0.02 gfcm$^2$/cm to about 0.05 gfcm$^2$/cm;
a cosmetic composition comprising an effective amount of a skin active agent; and
a pressure sensitive adhesive.

In yet another aspect a beauty care product is provided comprising:
a multi-layered barrier patch comprising:
  (i) a non-foamed first layer comprising a non-foamed polymer film having a first surface, and having a thickness from about 5 microns to about 250 microns, preferably from 10 microns to 40 microns; and preferably the first layer comprises ethylene vinyl acetate;

(ii) a foamed second layer comprising a foamed polymer film comprising a Mean Void Volume Percentage from about 45% to about 80%, preferably from about 50% to about 75%, more preferably from about 55% to about 73%, and a thickness of from about 10 microns to about 250 microns, preferably from about 40 microns to about 160 microns; and preferably the second layer comprises ethylene vinyl acetate;

a cosmetic composition comprising an effective amount of a skin active agent; and a pressure sensitive adhesive.

A method of treating skin is also provided and comprises:

a. applying a cosmetic composition to a target area of the skin, comprising an effective amount of a skin active agent;

b. applying a multi-layered barrier patch to the target area of skin, wherein the barrier patch is adjusted to comprise:
  (i) a non-foamed first layer comprising a non-foamed polymer film having a first surface, and having a thickness from about 5 microns to about 250 microns, preferably from 10 microns to 40 microns; preferably the first layer comprises ethylene vinyl acetate and preferably wherein the non-foamed first layer is substantially free of pigments;
  (ii) a foamed second layer comprising a foamed polymer film comprising a Mean Void Volume Percentage from about 45% to about 80%, preferably from about 50% to about 75%, more preferably from about 55% to about 73%, and a thickness of from about 10 microns to about 250 microns, preferably from about 40 microns to about 160 microns; and preferably the second layer comprises ethylene vinyl acetate;

wherein the cosmetic composition is at least partially in contact with the barrier patch.

Beauty care products herein are those useful for treatment of and application to keratinous tissue.

BRIEF DESCRIPTION OF THE DRAWINGS

While the specification concludes with claims that particularly point out and distinctly claim the invention, it is believed that the present invention will be better understood from the following description of aspects, taken in conjunction with the accompanying drawings in which:

DETAILED DESCRIPTION OF THE INVENTION

Figure 1:
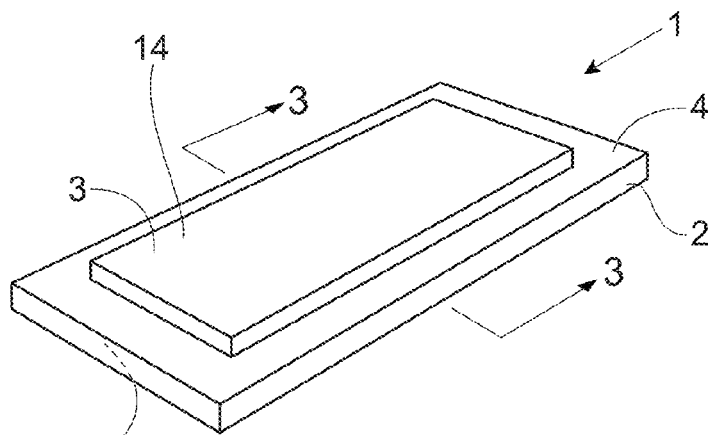
FIG. 1 is a perspective view of a beauty care product comprising a barrier patch, as shown and described herein.

While the specification concludes with the claims particularly pointing out and distinctly claiming the invention, it is believed that the present invention will be better understood from the following description.

In all aspects, all percentages are by weight of the composition (or product or barrier patch), unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. The term "molecular weight" or "M.Wt." as used herein refers to the number average molecular weight unless otherwise stated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "apply" or "application" as used in reference to a composition, means to apply or spread the compositions of the present invention onto a substrate such as the human skin surface or epidermis.

The term "dermatologically acceptable," as used herein, means that the compositions or components thereof so described are suitable for use in contact with mammalian keratinous tissue without undue toxicity, incompatibility, instability, allergic response, and the like.

The term "facial skin surface" as used herein refers to one or more of forehead, periorbital, cheek, perioral, chin, and nose skin surfaces. While facial skin surfaces are of concern and are exemplified herein, other skin surfaces may be treated with the compositions and methods of the present invention, for example, surfaces typically not covered by clothing such as facial skin surfaces, hand and arm skin surfaces, foot and leg skin surfaces, and neck and chest skin surfaces (e.g., décolletage).

The term "keratinous tissue", as used herein, refers to keratin-containing layers disposed as the outermost protective covering of mammals (e.g., humans, dogs, cats, etc.) which includes, but is not limited to, skin, mucosa, lips, hair, toenails, fingernails, cuticles, hooves, etc.

The terms "topical application", "topically", and "topical", as used herein, mean to apply (e.g., spread, spray) the compositions of the present invention onto the surface of the keratinous tissue.

As used herein, "effective amount" means an amount of a compound or composition sufficient to significantly induce a positive keratinous tissue benefit, including independently or in combination with other benefits disclosed herein. This means that the content and/or concentration of agent in the formulation is sufficient that when the formulation is applied with normal frequency and in a normal amount, the formulation can result in the treatment of one or more undesired keratinous tissue conditions (e.g., skin wrinkles). For instance, the amount can be an amount sufficient to inhibit or enhance some biochemical function occurring within the keratinous tissue. This amount of the skin care agent may vary depending upon the type of product, the type of keratinous tissue condition to be addressed, and the like.

The term "safe and effective amount" as used herein means an amount of a compound or composition sufficient to significantly induce a positive benefit, preferably a positive keratinous tissue appearance, including independently or in combinations with the benefits disclosed herein, but low enough to avoid serious side effects, i.e., to provide a reasonable benefit to risk ratio, within the scope of sound judgment of the skilled artisan.

As used herein, the term "water impermeable" includes materials or objects through which water in its liquid state does not pass.

The term "substantially free of" refers to an amount of a material that is less than 1%, 0.5%, 0.25%, 0.1%, 0.05%, 0.01%, or 0.001% by weight of composition, the barrier patch, and/or the layer of the barrier patch. "Free of" refers to no detectable amount of the stated ingredient or thing.

"Bio-based content" refers to the amount of carbon from a renewable resource in a material as a percent of the mass of the total organic carbon in the material, as determined by ASTM D6866-10, Method B. Note that any carbon from inorganic sources such as calcium carbonate is not included in determining the bio-based content of the material.

"Biodegradation" refers to a process of chemical dissolution of materials by microorganisms or other biological means.

"Bio-identical polymer" refers to polymers that are made from monomers where at least one monomer is derived from renewable resources. For instance, a bio-identical polyolefin is made from olefins that are derived from renewable resources, whereas a petro-based polyolefin is made from olefins typically derived from non renewable oil or gas.

"Bio-new polymer" refers to polymers that are directly derived (i.e., no intermediate compound in the derivation process) from renewable resources. Such renewable resources include cellulose (e.g. pulp fibers), starch, chitin, polypeptides, poly(lactic acid), polyhydroxyalkanoates, and the like.

"Monomeric compound" refers to an intermediate compound that may be polymerized to yield a polymer.

"Petrochemical" refers to an organic compound derived from petroleum, natural gas, or coal.

"Petroleum" refers to crude oil and its components of paraffinic, cycloparaffinic, and aromatic hydrocarbons. Crude oil may be obtained from tar sands, bitumen fields, and oil shale.

"Polymers derived directly from renewable resources" refer to polymers obtained from a renewable resource without intermediates. Typically, these types of polymers would tend be "bio-new".

"Post-consumer recycled polymers" refer to synthetic polymers recovered after consumer usage and includes recycled polymers from plastic bottles (e.g., laundry, milk, and soda bottles).

"Renewable resource" refers to a natural resource that can be replenished within a 100 year time frame. The resource may be replenished naturally, or via agricultural techniques. Renewable resources include plants, animals, fish, bugs, insects, bacteria, fungi, and forestry products. They may be naturally occurring, hybrids, or genetically engineered organisms. Natural resources such as crude oil, coal, and peat which take longer than 100 years to form are not considered to be renewable resources.

Mean Void Volume Percentage

One aspect of the invention provides a multi-layered barrier patch having at least 1 foamed layer having a defined Mean Void Volume Percentage. The technique for measuring Mean Void Volume Percentage is described herein. This method essentially describes the volume of the foamed layer occupied by voids. In other words, it describes the amount or degree of foaming of the foamed layer to allow one skilled in the art to differentiate between films of varying degrees of foaming. Generally, the more foaming, the greater percentage of voids, and thus a greater Mean Void Volume Percentage. The degree of foaming of a foamed layer may be characterized by a Mean Void Volume Percentage, as determined by X-ray micro-computed tomography (as described herein) or simply "microCT."

In one aspect, the foamed layer comprises from 45% to 80% of a Mean Void Volume Percentage (relative to the volume of the foamed layer in total), preferably from 50% to 75%, more preferably from 55% to 73%, Mean Void Volume Percentage.

Flop Index

One way of describing the special visual effect of the barrier patch or product herein is from the angle dependent light reflection (or "glossiness") and color luminosity (or "L"). A non-flat surface provides different angles to certain incident light and thus the reflected light provides different glossiness and L in different areas of the surface. This difference in glossiness and reflection can be measured via the method described below:

The flop index or "FI" is the characterization of color luminosity change and the degree of pearlescence and can be mathematically calculated by the following formula:

$$\text{Flop Index} = \frac{2.69(L^*_{15°} - L^*_{110°})^{1.11}}{(L^*_{45°})^{0.86}};$$

wherein an incident light that is 45° to the surface, and the mirror reflection direction is symmetrically on the other side of the normal line which is perpendicular to the surface. $L^*_{15°}$ describes the luminosity at the angle which is 15° to the normal line from the reflection direction, and $L^*_{110°}$ is 110° to the normal line from the reflection direction. $L^*_{45°}$ is the normal line which is perpendicular to the surface. Flop index indicates the L changes with different observation angles and higher FI means more dark and light contrast and thus more evident effect.

FI can be measured following ASTM E2539. Suitable measuring device includes multi angle photometer MA98 from X-rite Company.

One aspect of the invention provides for a multi-layer barrier patch having a FI of at least 2, more preferably at least 2.5, yet more preferably at least 3.0, yet still more preferably at least 3.5 according to ASTM E2539. In another aspect of the invention the multi-layer barrier patch has a FI of from about 2.5 to about 15, more preferably from about 2.5 to about 6, or from about 2.5 to about 5.5, yet more preferably from about 3.0 to about 5.0, according to ASTM E2539.

One aspect of the invention provides for a multi-layer barrier patch having a Gloss of about 8 to about 40, in another aspect from about 11 to about 35, and in another aspect about 12 to about 30, measured according to the Gloss method herein.

WVTR

According to one aspect, the multi-layered barrier patch has an WVTR value between about 1 g/m$^2$/24 h to about 500 g/m$^2$/24 h, and in another aspect has a WVTR from about 1 g/m$^2$/24 h to about 250 g/m$^2$/24 h and/or from about 1 g/m$^2$/24 h to about 1.80 g/m$^2$/24 h and/or from about 2 g/m$^2$/24 h to about 150 g/m$^2$/24 h and/or from about 2 to about 20 g/m$^2$/24 h. The term WVTR stands for "Water Vapor Transmission Rate", i.e. the amount of vapor which can pass per unit area during a certain period of time.

The multi-layered barrier patch in certain aspects is non-porous or impermeable to water. In certain other aspects the multi-layered barrier patch is impermeable to the cosmetic composition, the skin care active agent employed, and fluids wherein the WVTR is from about from about 2 to about 100 g/m$^2$/24 h. While not being bound by theory using a multi-layered barrier patch that prevents water loss from the cosmetic composition while the cosmetic composition is in contact with the keratinous tissue and skin, prevents the cosmetic composition from drying out. Water loss from the cosmetic composition may lower the water concentration, may destabilize an emulsion if present, and may increase the concentration of skin active agents. This may result in reduced or loss of efficacy and/or irritation to the skin.

Such relative water impermeability and lower water vapor permeability of the multi-layered barrier patch may increase the effectiveness and efficiency of the cosmetic composition used with the barrier patch. For example, without being bound by theory, the water impermeability and lower vapor permeability of the multi-layered barrier patch employed serves to increase the penetration of the skin care active agent into the skin.

In certain aspects the multi-layered barrier patch may, for example, consist of a perforated polyolefin film, where the size of the holes has been chosen so that air and vapor may pass, but not liquid molecules. Breathable materials can, as mentioned above, consist of perforated plastic films. One example of such film is described in U.S. Pat. No. 5,628,737 and/or micro-porous plastic films, as is described in, for example, EP-A-0238200. These laminates and films, however, are not preferred herein due to their relatively high WVTR and higher levels of breathability.

Multi-Layered Barrier Patch

The multi-layered barrier patch may be a co-extruded film laminate comprising at least two layers, but can comprise 3, 4, 5, 6, or more layers. In a preferred aspect, the multi-layered co-extruded film barrier patch has at least three layers, and is preferably a ethylene vinyl acetate ("EVA") comprising film. In a preferred aspect, a foamed layer is in-between layers of non-foamed layers, e.g. the first layer and the third layer, on either side.

In certain aspects, multi-layer barrier patch is generally made of a flexible film material which is capable of remaining fitted and flexing during the movement of the human body and movements especially associated with facial expressions or gestures. By "flexible" it is meant that the multi-layer harrier patch may be substantially bent or folded without breaking, tearing, ripping, etc. The multi-layer barrier patch may comprise a flexibility from about 0.009 gfcm$^2$/cm to about 0.14 gfcm$^2$/cm and/or about 0.01 gfcm$^2$/cm to about 0.055 gfcm$^2$/cm, and/or from about 0.02 gfcm$^2$/cm to about 0.05 gfcm$^2$/cm, according to the Flexibility method provided herein. In an aspect the multi-layer barrier patch also does not collapse or fold under gravity or upon handling and application by the user. It is desirable for the multi-layer film to conform to the target area of the skin surface to which it is applied without folding, crinkling, or inducing more wrinkling of the target area of the skin. Accordingly, the barrier patch is readily conformable to the skin and remains flexible throughout the duration of use, as the user moves during the period of time worn.

In an aspect the barrier patch or product comprises a Surface Roughness (Ra) from about 3 to about 30, or from about 4 to about 29, or from about 10 to about 28, according to the Surface Roughness method herein.

Figure 2:
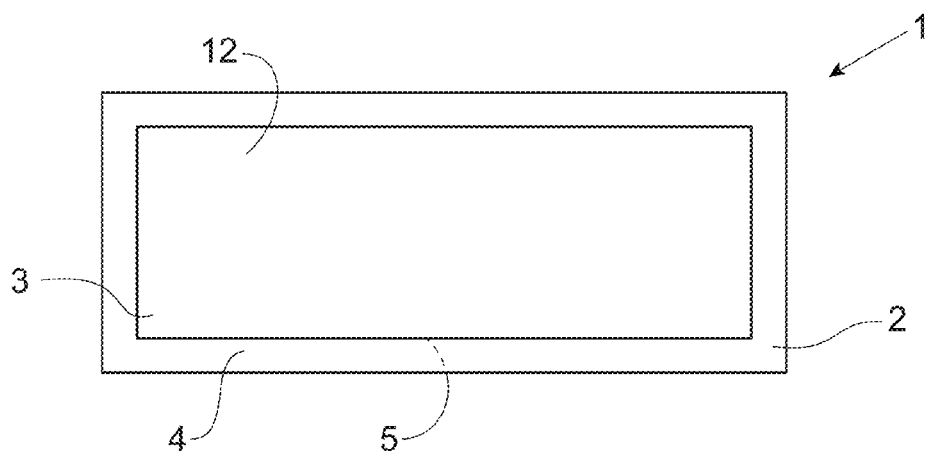
FIG. 2 is a top plan view of the product of FIG. 1.
Figure 3:
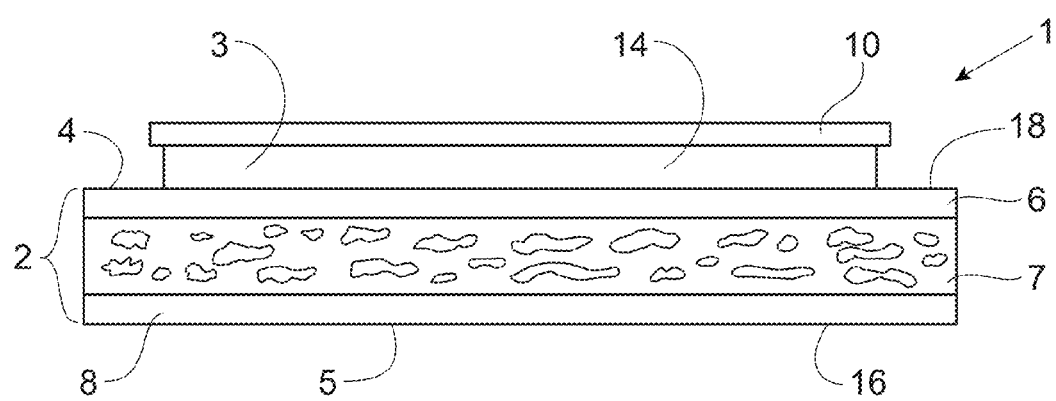
FIG. 3 is a cross section view of the product of FIG. 1 taken along 3-3 of FIG. 1, further comprising a release layer.

Exemplary aspects of the beauty care product or product 1 are shown in FIGS. 1, 2 and 3. FIGS. 1 and 2 show a product comprising a barrier patch 2 and a pressure sensitive adhesive 3. The barrier patch has a first surface 4 and a second surface 5. The pressure sensitive adhesive 3 is in contact with at least part of the first surface 4 of the barrier patch 2 to form a pressure sensitive adhesive coated region 12 of the first surface 4. The product 1 may further comprise a cosmetic composition 14 comprising an effective amount of a skin active agent. In one aspect the adhesive 3 comprises the cosmetic composition. In other aspects the cosmetic composition 14 is distributed to some extent and/or homogeneously distributed throughout the pressure sensitive adhesive. In another aspect the pressure sensitive adhesive 3 is separated from the cosmetic composition or the cosmetic composition is a separate layer from the layer of pressure sensitive adhesive or the pressure sensitive adhesive is substantially free of the cosmetic composition 14.

In the aspect of FIGS. 1, 2 and 3, the product 1 and barrier patch 2 are rectangular; however this shape is not intended to limit the invention.

FIG. 3 shows a cross section of product 1 comprising a barrier patch 2 and a pressure sensitive adhesive 3. The barrier patch 2 has a first surface 4 and a second surface 5. The pressure sensitive adhesive 3 is in contact with at least part of the first surface 4 of the barrier patch 2 to form a pressure sensitive adhesive coated region 12 of the first surface 4. The barrier patch 2 further comprises a non-foamed first layer 6, a foamed second layer 7 and a non-foamed third layer 8. In an aspect the non-foamed third layer 8 and the second surface 5 comprise a consumer facing layer or consumer facing surface 16. The first surface 4 and the non-foamed first layer 6 are a non-consumer facing surface 18 and a non-consumer facing layer. The barrier patch further comprises a release layer 10.

In an aspect the barrier patch and/or product is substantially free of pigments. As used herein "pigment" means a dye, colorant or pigment material that provides color to the barrier patch or product. The barrier patch or product may be colored by the use of suitable dyes and pigments, which may be selected from the group consisting of organic pigments, inorganic pigments, interference pigments, lakes, natural colorants, pearlescent agents, dyes, and mixtures thereof. In an aspect the pigments, lakes and/or dyes are hydrophobic. Other dyes and pigments are disclosed in *International Cosmetic ingredient Dictionary and Handbook*, 10$^{th}$ Edition, Volume 3, 2004, Colorants, pp. 2194-2197. In another aspect one or more of the non-foamed layer and/or foamed layers are substantially free of pigments. In yet another aspect the non-foamed layer that is a consumer facing layer and not in contact with the pressure sensitive adhesive, such as the non-foamed third layer 8, is substantially free of pigments. In an aspect the optical effects, or the Flop Index, of the barrier layer or product is achieved without the use of pigments.

The barrier patch 2 of the present invention may comprise a solid sheet material. The sheet provides the primary structure and shape to the patch, allowing it to be handled and applied for treatment of a specific target area of the skin. In another aspect the solid sheet or barrier patch is self supporting.

The layers of the barrier patch may comprise at least one material that includes but is not limited to polypropylene (PP); polyethylene (PE), metallocene plastomers, metallocene elastomers, high density polyethylene (HDPE), rubber modified LDPE, rubber modified LLDPE, acid copolymers, polysytyrene, cyclic polyolefins, polyethylene terephthalate (PET); polyvinylchloride (PVC); polyamide (PA); polycarbonate; polyurethane; cellulose acetate; polychloropene; polysulfone; polytetrafluoroethylene (PTFE); polyvinyl acetate (PVA); polyethylene glycol terephthalate film; polystyrene; polyphenylene oxide (PPO); acrylonitrile butadiene styrene (ABS); acrylic; acrylonitrile styrene acrylate (ASA); ethylene vinyl alcohol, natural rubber, latex, nylon, nitrile, silicone and thermo plastic elastomers (TPE), ethylene vinyl acetate (EVA), ethylene acrylic acid (EAA), copolymers of PE with PP, bimodal resins, any of which may be from either homopolymers or copolymers, and blends and combinations of these materials. Blends may be physical blends or reactor blends. The layers may comprise a single polymer or mixtures of polymers or copolymers. Laminates of these layer materials may also be used.

In an aspect the foamed second layer comprises a combination of PE and EVA. The foamed second layer may comprise from about 15% to about 40%, or from about 20% to about 35% of PE and from about 60% to about 85%, or about 65% to about 80% EVA.

Film additives are further detailed in U.S. patent publications from U.S. patent application Ser. No. 13/924,983, filed Jun. 24, 2013 (P&G US 2014/0376835; Case 12966Q); and U.S. patent application Ser. No. 13/924,999, filed Jun. 24, 2013 (P&G Case 12967Q), and the references cited therein.

For example the film layer of the barrier patch optionally can include an additive such as a slip agent or an antistatic agent (e.g., euracamide, a steramide), a filler (e.g., talc, clay, pulp, titanium dioxide, thermoplastic starch, raw starch wood flour, diatomaceous earth, silica, inorganic glass, inorganic salts, pulverized plasticizer, pulverized rubber), a pigment (e.g., mica, titania, carbon black), a UV inhibitor, an anti-coloring agent, a mold release agent, a flame retardant, an electrically conductive agent, an antioxidant, an impact modifier, a stabilizer (e.g., a UV absorber), wetting agents, carbon, graphene and a biodegradable-enhancing additive (e.g., an oxo-degradable additive or an organic material). An oxo-degradable additive is often compounded into a polymer in a concentration of about 1 wt. % to about 5 wt. %, based on the total weight of the polymer, and includes at least one transition metal that can foster oxidation and chain scission in plastics when exposed to heat, air, light, or mixtures thereof. Organic materials (e.g., cellulose, starch, ethylene vinyl acetate, and polyvinyl alcohol) also can be used as biodegradable-enhancing additives, although they cannot promote degradation of the non-degradable portion of the polymer matrix.

A color masterbatch containing pigment and/or slip/antiblock agents and/or liquid colorants can also be added to afford certain aesthetics and functionality.

Pigments if present may be typically be used in concentrations of about 0.5 wt. % to about 15 wt. %, and/or from about 1 wt. % to about 10 wt. %, or from 1.5 wt. % to about 7 wt. %, based on the total weight of the polymer.

A preferred material for one or more of the layers includes ethylene vinyl acetate, EVA (CAS No. 24937-78-8) copolymer. Different grades of EVAs tend to have different ethylene-to-vinyl acetate monomer ratios and/or different melt indices (molecular weights). For example the percentage of VA monomer may range from about 20% to about 50% or from about 25% to about 40% of VA or from about 25% to about 30% of VA. For example the melt flow index may range from about 0.7 dg/min to about 60 dg/min and/or from about 2 dg/min to about 6 dg/min and/or from about 2 dg/min to about 4 dg/min. EVA grades useful herein include Dupont Elvax® Grades: 260 (28% VA; Melt Flow Index-MFI 6 dg/min via ASTM D1238); Grade 250 (28% VA; MFI 25 dg/min); Grade 150 and 150 W (32% VA; MFI 43 dg/min); Grade 40 W (40% VA; MFI 52 dg/min); and Celanese Ateva® 2803G (28% VA; MFI 3 dg/min via ASTM D1238) and Ateva® 1807EG (18% VA; MFI 0.7 dg/min). In an aspect the ethylene vinyl acetate polymer may have an ethylene-to-vinyl acetate monomer ratio of about 4:1 to about 1:1, preferably the ratio may be from about 3:1 to about 3:2.

In an aspect the multi-layer barrier patch comprises three layers, e.g. a foamed second layer comprising EVA and a layer of non-foamed EVA on either side, i.e., a first non-foamed EVA layer and a third non-foamed EVA layer wherein the foamed EVA layer is in-between said first and third non-foamed layers.

In one aspect the multi-layer barrier patch is substantially free of a non-woven material.

In another aspect the multi-layer barrier patch includes a cornea treatment.

The film layers herein may comprise polyethylene. The term "polyethylene" or "PE" is used herein the broadest sense to include PE of any of a variety of resin grades, density, branching length, copolymer, blend, catalyst, and the like. The layer may comprise a blend of different grades of polyethylene, that may include LLDPE, LDPE, VLDPE, HDPE, or MDPE, or combinations thereof; manufactured using Ziegler-Natta catalysts, Chromium catalysts, metallocene based catalysts, single site catalysts, and other types of catalysts. The polymers may be homopolymers or copolymers. Blends may be physical blends or reactor blends. These materials can be bio-based, petro-based and recycled/reground. LLDPE copolymers can be made with any one or more of butene, hexene and octene comonomers. The ratio of the different grades can vary.

The material composition and/or polymer resins used in the foamed layer may be different from those used in the non-foamed layer(s), since the material composition and/or resins may be optimized for foam formation, or other film layer properties. Additives, particularly small amount of nucleating agents selected from the group consisting of $CaCO_3$, clays, talcs, and combinations thereof, may be included for quick bubble formation during foaming process.

The resin used in making the layers of the barrier patch may include renewable materials, either "bio-identical" or "bio-new" materials, or a combination thereof. Some non-limiting options of applicable bio-identical and/or bio-new materials are further detailed in U.S. Ser. No. 13/924,983, filed Jun. 24, 2013 (P&G US Publication Number 2014/0376835), at pages 15-22; and U.S. Ser. No. 13/924,999, filed Jun. 24, 2013 (P&G US Publication No. 2014/0377512 A1; P&G Case 12967Q) at pages 12-20. For example the barrier patch may include at least one layer made of a plastic resin. The resin could be a traditional petro-based polyolefin, or it could be a renewable based polyolefin, or a blend thereof. Alternatively it could be a blend comprising a petro-based or renewable based polyolefin blend mixed with a renewable "bio-new" material that is chemically different from traditional petro-based polyolefins. The film layer could be comprised of a material or mixture of materials having a total bio-based content of about 10% to about 100% using ASTM D6866-10, method B. In one aspect, the layer may comprise from about 5% to about 99% by weight of a polymer (A) comprising at least one or possibly more of a low density polyethylene (LDPE), ethylene vinyl acetate (EVA), a linear low density polyethylene (LLDPE), a high density polyethylene homopolymer/high density polyethylene copolymer, a medium density polyethylene, a very low density polyethylene (VLDPE), a plastomer, a polypropylene/copolypropylene/heterophasic polypropylene, polyethylene terephthalate (PET), PLA (e.g., from Natureworks), polyhydroxyalkanoate (PHA), poly(ethylene-2,5-furandicarboxylate) (PEF), cellulose (available from, for example, Innovia), NYLON 11 (i.e., Rilsan® from Arkema), starch (either thermoplastic starch or starch fillers), bio-polyesters, (e.g., those made from bioglycerol, organic acid, and anhydride, as described in U.S. Patent Application No. 2008/0200591, incorporated herein by reference), polybutylene succinate, polyglycolic acid (PGA), and polyvinyl chloride (PVC). At least one of the constituents of polymer (A) may be at least partially derived from a renewable resource. Recycled materials may also be in added. In specific cases, materials that are biodegradable may be utilized.

Some of the "bio-new" materials may further contribute to reflectivity of the film, as the presence of this additional material within the film layer structure can lead to additional light reflectivity, due to their typical incompatibility with the polyolefin matrix.

Thickness

In one aspect, the total thickness of the multi-layered co-extruded film barrier patch is from 20 microns to 500 microns, preferably from 50 microns to 200 microns, more preferably from 70 to 180 microns, yet more preferably from 75 to 150 microns, and combinations thereof. Scanning electron microscopy (SEM) is one technique of measuring thickness.

Another aspect of the invention provides for the foamed second layer having a thickness from 10 microns to 250 microns, preferably from 40 microns to 160 microns, or from 40 microns to 90 microns, more preferably from 40 microns to 60 microns and combinations thereof.

Another aspect of the invention provides for each of the non-foamed first and/or third layers having a thickness from 5 microns to 250 microns, preferably from 5 microns to 90 microns, more preferably from 10 microns to 40 microns, and combinations thereof.

In an aspect the thickness of the foamed second layer is greater than the thickness of one or both of the non-foamed first layer and the non-foamed third layer.

In an aspect the basis weight for the barrier patch (without the adhesive) is from 40 gsm to 190 gsm, for instance 45 gsm to 170 gsm and/or from 50 gsm to 140 gsm.

Method of Foaming the Resin

The foam can be imparted to the foamed layer by several ways. Generally, physical foaming is provided by injecting air or an inert gas (typically $N_2$ or $CO_2$ although another gas could be considered) into the resin during an extrusion process. A uniform, small-cell bubble structure may be achieved by the adding of the inert gas, during the extrusion process. The inert gas may be delivered to the extruder and under pressure in the extruder is mixed with the polymer. The goal is to produce a substantially homogeneous mixture. A pressure drop during extrusion occurs and a phase separation results providing uniformly distributed small cells or bubbles throughout the material. The formation of individual cells may enhanced by the fillers mentioned herein. The gas preferably may be provided preferably at levels of about 0.02 and 0.25% by weight. During co-extrusion, the foam-forming substance, e.g. the inert gas, may be added to only a single layer or part of a layer.

Chemical means (wherein gas is produced on heating, e.g., use of inorganic material, such as the foaming agents marketed by the Clariant Corporation) may also be used. An example of foaming agent chemistry includes Sodium Hydro Carbonate Powder and an acidifier within a master batch of resin added prior to heating of the resin. Upon heating, chemical blowing agents release carbon dioxide. The carbon dioxide expands and forms bubbles in the film during subsequent processing steps. One exemplary chemical equation describing the transition of the blowing agent to carbon dioxide is:

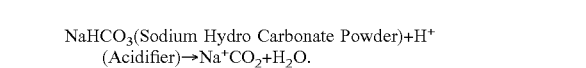

$NaHCO_3$(Sodium Hydro Carbonate Powder)+$H^+$ (Acidifier)→$Na^+CO_2$+$H_2O$.

Of course, other methods may be employed in the practice of the present invention, such as, for example, through the incorporation of hard particles (e.g. $CaCO_3$ or PS or PLA or TPS or other minerals) followed by stretching (uni-axial or bi-axial) of the film to cavitate around the particles. Another method is typically called "Solid State Foaming", using gas saturation of preformed films, such as that practiced by the University of Washington, U.S.A. See publications from Professor Kumar.

As mentioned herein the foamed layer may comprise a filler of organic particles. These may be provided to aid in nucleation, for example aid the formation of a greater number of small cells. Fillers such as talc, chalk, clay, pulp, titanium dioxide, etc. may be present in foamed layer at a concentration from about 5 wt. % to about 20 wt. % or 30 wt. %.

Foaming methods are described in U.S. Pat. No. 6,051,174; WO 1998/008667 (U.S. Pat. No. 6,284,810); WO 2001/089794 (U.S. Pat. No. 6,593,384); WO 2002/014044 (U.S. Pat. No. 6,616,434) and WO 2004/039552 (U.S. Pat. No. 7,144,532). The MuCell® foaming method, is also an example, and devices for this method are marketed by Trexel Inc., USA.

The foam bubbles that are produced are generally at a micrometer or nanometer scale. In some executions, the foam bubbles are in hundreds of microns in range in the length and width while others can be up to several mm long.

Non-limiting examples of how to provide foamed films is described in U.S. Pat. Nos. 6,005,013; 6,284,810; 6,602,064; and U.S. Pat. No. 8,263,206; and U.S. Pat. Publ. Nos: US 2008/0138593 A1; US 2012/0228793 A1. A supplier of a multi-layered co-extruded film is Mondi Consumer Packaging Technologies GmbH in Gronau. A branded technology from Mondi for making foamed film includes Nor® Cell technology. See also US 2014/0079938 A1.

For multi-layered barrier patches where one or more layers are made of different polymers, the layers may be co-extruded. Single layer films may also be laminated to create the multilayer barrier patch. The lamination processes include, for example, dry lamination, solventless lamination, and extrusion lamination. In one aspect, the laminate comprises an adhesive layer adhering the multi-layered extruded film and the printed thermoplastic layer; preferably wherein the adhesive is polyurethane-based for solvent-less lamination, and for dry lamination, the adhesive could be polyurethane-based (dissolved in organic solvents) or acrylic acid-based (dissolved in water). Solvent-based dry lamination typically uses a two component polyurethane adhesive. Water-based dry lamination typically uses acrylic based adhesives. Solvent-less lamination typically use a one or two component polyurethane adhesive. One example of such the 2-component PU adhesive for solvent-less lamination is MOR-FREE™ 706A/Coreactant C-79 from Dow Chemical where MOR-FREE™ 706A provides the NCO component and the Coreactant C-79 provides the OH component for the formation of polyurethane. The adhesives may also be either "bio-identical" or "bio-new" materials. See e.g., Dow Chemical's soy-based polyol adhesives.

Where appropriate the barrier patch may be laminated by heat welding (which may further include the use of pressure, ultrasonic forces and radio or high frequencies), co-extrusion; adhesives, electro static adhesions (such as flocking by fibres) and topical surface applications.

Adhesives

A variety of adhesives may be used in the manufacture of the barrier patch herein. Typically, the adhesive material is a pressure-sensitive adhesive (PSA) that is suitable for long-term skin contact, and which should be physically and chemically compatible with the non-foamed first and/or foamed second layer and/or additives that are present. Examples of suitable adhesive materials include, but are not limited to, the following: acrylic and methacrylic ester homo- or copolymers, butyl rubber based systems, silicones, urethanes, vinyl esters and amides, olefin copolymer materials, natural or synthetic rubbers, hot-melt adhesives (see, for example, U.S. Pat. No. 5,387,450); polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene) and combinations thereof.

According to one aspect the adhesive is a hotmelt adhesive including adhesives selected from the group consisting of EVA, metallocene polyalphaolefins, polyolefins including atactic polyalphaolefins, block copolymers such as diblocks copolymers and triblock copolymers, polyurethane hot melts, polyamides and combinations thereof. In one aspect the adhesive comprises diblock copolymers, triblock copolymers and combinations thereof. Diblocks and triblock copolymers may include styrene/isoprene; styrene/butadiene; butylene/ethylene/styrene; and combinations thereof.

High viscosity triblock copolymers may be used as adhesives and have the configuration A-B-A wherein the polymer blocks A are non-elastomeric polymer blocks which, as homopolymers have glass transition temperatures above 20° C. The elastomeric polymer blocks, B, are generally isoprene or butadiene which may be partially or substantially hydrogenated or mixtures thereof. Further, the copolymers may be linear or branched.

Diblock copolymers may generally have the A-B configuration where A and B are as described previously.

Liquid diluents may be added to the adhesive compositions. The adhesive composition may comprise from about 60% to about 99% diluents, by weight. In an aspect the majority of the liquid diluent is oil. Preferably the liquid diluent comprises, or consists essentially of, oils such as highly refined white petroleum mineral oil. Useful diluents are primarily aliphatic in character and compatible with the polymer midblock. Plasticizers may also be included, e.g. paraffinic and naphthenic petroleum oils, highly refined aromatic-free paraffinic and naphthenic food and technical grade oils, highly refined white petroleum mineral oils, and liquid tackifiers such as the synthetic liquid oligomers of polybutene, polypropene, polyterpene, etc. The synthetic process oils may be high viscosity oligomers which may be permanently fluid/liquid monoolefins, isoparaffins or paraffins of moderate to high molecular weight.

In an aspect the adhesive is selected from the TECHNOMELT® and DERMA-TAK® brands available from Henkel, for example TECHNOMELT PSM 154A DERMA-TAK®. DERMA-TAK products are pressure-sensitive adhesives that are generally used with films to adhere to the skin and encompass both solvent-based acrylic and formulated rubber (liquid and hotmelt) pressure-sensitive adhesives. Useful adhesives may also be selected from those described in U.S. Pat. Nos. 6,448,303 and 5,559,165.

The adhesive typically has an average thickness ranging from about 0.5 mils to about 15 mils, in alternative aspects about 1 mils to about 5 mils.

Release Layer

The barrier patch or product herein may further optionally comprise a protective release layer removably attached to the pressure sensitive adhesive or the pressure sensitive adhesive side of the barrier patch. The release layer provides protection for the pressure sensitive adhesive from the environment and prior to application by the user.

The protective release layer may comprise materials including polymer resins such as a polyolefins e.g. polypropylene (including stratified biaxially oriented polypropylene (SBOPP)), polyethylene (including LDPE; LLDPE; HDPE; Metallocene) or polyethylene terephthalate, and combinations thereof. Alternative materials which may be used include polyvinylchloride, polyamide, acetyl, acrylonitrile butadiene styrene, acrylic, acrylonitrile styrene acrylate, ethylene vinyl alcohol, ethylene vinyl acetate, nylon, latex, natural or synthetic rubbers, polycarbonate, polystyrene, silicone or thermo plastic elastomer, thermo plastic vulcanate or copolymers of said materials, and combinations thereof. Where appropriate the protective release layer may comprise one or more laminations, or combinations of multiple layers. In an aspect the protective release layer may comprise a coating of a non-stick material. Exemplary non-stick coatings include wax, silicone, fluoropolymers such as TEFLON®, and fluorosilicones.

In an aspect, the protective release layer covers the entire aforementioned area of pressure sensitive adhesive coated region of the barrier patch layer. In another aspect the protective release layer is water impermeable. In a further aspect, the release layer has a mean thickness of at least about 50 microns, or at least about 85 microns, or from about 70 microns to about 150 microns, and/or from about 90 microns to about 120 microns.

The release layer may optionally extend, in whole or part, beyond the pressure sensitive adhesive coated region of the layer. The release layer may extend partially beyond layer to provide a removal tab that facilitates ease of removal of the release layer.

Size and Shape of Multi-Layer Barrier Patch

The barrier patch or product may have a size and shape adapted to conform to a desired target area of skin which could be a human face or part thereof, legs, hands, arms, feet, or human torso. They are generally flat in appearance.

The exact size and shape of the barrier patch or product will depend upon the intended use and product characteristics. The barrier patch or product herein can be, for example, a square, circle, semicircle, rectangle, triangle, oval, ring, crescent, crescent with rounded corners, teardrop or other more complex and irregular shape. The shape of the barrier patch or product may be selected from the group consisting of circle, square, rectangle, triangle, and/or irregular shape that conforms to the contours of the forehead, perioral, and/or periorbital areas of the human face.

In certain other aspects, the harrier patch or product comprises a size and shape to treat different areas of the face such as the forehead, the under eye area and the under eye area combined with the crows feet area around the eye. Thus the size of the barrier patch or product may be determined by the size of the target area of skin to be treated. Thus a barrier patch or product shaped to fit the face or the target area of skin, may have a surface area from about 0.25 cm$^2$ to about 50 cm$^2$, and/or from about 1 cm$^2$ to about 30 cm$^2$, and/or from about 1 cm$^2$ to about 20 cm$^2$, and/or from about 1 cm$^2$ to about 1.5 and/or from about 5 cm$^2$ to about 15 cm$^2$. Surface area refers to that of a flat plane having the same boundary as the surface, i.e. ignoring any surface texturing present.

In certain aspects the barrier patch is substantially free of, comprises only non-effective amounts of, or is free of, a skin active agent. As such, the barrier patch of the present invention may be characterized as a "blank" barrier patch. In this regard, in an aspect an effective amount of the skin active agent is employed as a separate component from the barrier patch.

The product may remain in contact with the target area of skin for a period of time from about 2 hours to about 1 week. Once the period of time has elapsed, the barrier patch or product is removed by peeling it away from the target area of the skin so that upon removal, the barrier patch is removed intact, i.e., no barrier patch material is left on the target area of the skin.

Cosmetic Composition
Skin Active Agents

In one aspect the product provides an effective amount of a skin active agent to be delivered to the target area of skin that will provide a layer of the cosmetic composition having a thickness from about 10 microns to about 30 microns and/or from about 12 microns to about 25 microns. In another aspect the product provides from about 0.5 mg/cm2 to about 3 mg/cm2 of the cosmetic composition, and/or from about 1 mg/cm2 to about 2 mg/cm2 to the target area of skin. In one aspect and without being bound by theory, the use of the proper amount of the cosmetic composition will minimize the interaction of the cosmetic composition with the pressure sensitive adhesive. The cosmetic composition may also comprise an effective amount of a dermatologically acceptable carrier.

The compositions of the present invention may comprise a skin active agent which provides a particular skin care benefit characteristic of the usage of the skin care product. The skin care benefit may include benefits related to appearance or make-up of the skin. The skin care active can provide acute (immediate and short lived) benefits, or chronic (long term and longer lasting) benefits.

The term "skin active agent" as used herein, means an active ingredient which provides a cosmetic and/or therapeutic effect to the area of application on the skin. The skin active agents useful herein include skin lightening agents, anti-acne agents, emollients, non-steroidal anti-inflammatory agents, topical anesthetics, artificial tanning agents, anti-microbial and anti-fungal actives, skin soothing agents, sun screening agents, skin barrier repair agents, anti-wrinkle agents, anti-skin atrophy actives, lipids, sebum inhibitors, sebum inhibitors, skin sensates, protease inhibitors, anti-itch agents, desquamation enzyme enhancers, anti-glycation agents, diaper rash agents, anti-eczema agents, botanicals, and mixtures thereof. When included, the present composition comprises a safe and effective amount of a skin active agent and/or from about 0.0001% to about 20%, in another aspect from about 0.01% to about 10% of at least one skin active agent.

The cosmetic compositions may include from about 0.00001 to about 10% by weight of botanical actives or from about 0.01 to about 8 percent by weight, or from about 0.05 to about 5 percent by weight. "Botanical" herein means a substance, extract or derivative of a plant and may also be described as "herbals". Botanicals may include water-soluble or oil-soluble active materials extracted from a particular plant including materials extracted from *echinacea, yucca glauca*, willow herb, basil leaves, Turkish oregano, carrot root, grapefruit fruit, fennel fruit, rosemary, thyme, blueberry, bell pepper, black tea, blackberry, black currant fruit, Chinese tea, coffee seed, dandelion root, date palm fruit, gingko leaf, green tea polyphenols (e.g. epicatechin gallate and epigallocatechin 3-O-gallate), hawthorn berries, licorice, oolong tea, sage, strawberry, sweet pea, tomato, vanilla fruit, neohesperidin, quercetin, rutin, morin, myricetin, chlorogenic acid, glutathione, glycyrrhizin, absinthe, *arnica*, centella *asiatica*, chamomelle, comfrey, cornflower, horse chestnut, ivy (Herdera helix), *magnolia, mimosa*, oat extract, pansey, scullcap, seabuckthorn, white nettle, witch hazel and any combinations thereof.

The type and amount of skin active agents are selected so that the inclusion of a specific agent does not affect the stability of the composition. For example, hydrophilic agents may be incorporated in an amount soluble in the aqueous phase, while lipophilic agents may be incorporated in an amount soluble in the oil phase.

Other skin active agents purported to exhibit expression-line relaxing benefits for use in the present invention include, but are not limited to, Lavandox available from Barnet Products Corporation; Thallasine 2, available from BiotechMarine; Argireline NP, available from Lipotec; Gatuline In-Tense and Gatuline Expression, available from Gattefosse; Myoxinol LS 9736 from BASF Chemical Company, Syn-ake, available from DSM Nutritional Products, Inc.; and Instensyl®, available from Silab, Inc; Sesaflash™, available from Seppic Inc.

Skin lightening agents useful herein refer to active ingredients that improve hyperpigmentation as compared to pre-treatment. Useful skin lightening agents herein include ascorbic acid compounds, vitamin B3 compounds, azelaic acid, butyl hydroxyanisole, gallic acid and its derivatives, glycyrrhizinic acid, hydroquinone, kojic acid, arbutin, mulberry extract, and mixtures thereof. Use of combinations of skin lightening agents is believed to be advantageous in that they may provide skin lightening benefit through different mechanisms.

Ascorbic acid compounds useful herein include ascorbic acid per se in the L-form, ascorbic acid salt, and derivatives thereof. Ascorbic acid salts useful herein include, sodium, potassium, lithium, calcium, magnesium, barium, ammonium and protamine salts. Ascorbic acid derivatives useful herein include, for example, esters of ascorbic acid, and ester salts of ascorbic acid. Particularly preferred ascorbic acid compounds include 2-o-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phosphate ester salts such as sodium ascorbyl phosphate, potassium ascorbyl phosphate, magnesium ascorbyl phosphate, and calcium ascorbyl phosphate. Commercially available ascorbic compounds include magnesium ascorbyl phosphate available from Showa Denko, 2-o-D-glucopyranosyl-L-ascorbic acid available from Hayashibara and sodium L-ascorbyl phosphate with tradename STAY C available from Roche.

Vitamin $B_3$ compounds useful herein include, for example, those having the formula:

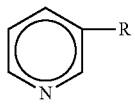

wherein R is —$CONH_2$ (e.g., niacinamide) or —$CH_2OH$ (e.g., nicotinyl alcohol); derivatives thereof; and salts thereof. Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Preferred vitamin $B_3$ compounds are niacinamide and tocopherol nicotinate, and in another aspect is niacinamide. In a preferred aspect, the vitamin $B_3$ compound contains a limited amount of the salt form and is more preferably substantially free of salts of a vitamin B3 compound. Preferably the vitamin $B_3$ compound contains less than about 50% of such salt, and is more preferably substantially free of the salt form. Commercially available vitamin $B_3$ compounds that are highly useful herein include niacinamide USP available from Reilly.

Other hydrophobic skin lightening agents useful herein include ascorbic acid derivatives such as ascorbyl tetraisopalmitate (for example, VC-IP available from Nikko Chemical), ascorbyl palmitate (for example available from Roche Vitamins), ascorbyl dipalmitate (for example, NIKKOL CP available from Nikko Chemical); other agents such as octa-decenedioic acid (for example, ARLATONE DIOIC DCA available from Uniquema); *oenothera biennis* sead extract, and *pyrus* malus (apple) fruit extract, Water and Myritol 318 and butylene glycol and tocopherol and sscorbil tetraisopalmitate and Paraben and Carbopol 980 and DNA/SMART-VECTOR UV available from COLETICA, magnesium ascorbyl phosphate in hyaluronic filling sphere available from COLETICA, and mixtures thereof.

Other skin active agents useful herein include those selected from the group consisting of N-acetyl D-glucosamine, panthenol (e.g., DL panthenol available from Alps Pharmaceutical Inc.), tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate: DL-α-tocopheryl acetate available from Eisai), azelaic acid, arachidonic acid, tetracycline, ibuprofen, naproxen, ketoprofen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof.

The compositions of the present invention in various aspects may comprise N-acyl amino acid compounds. Suitable N-acyl amino acid compounds include, but are not limited to, N-acyl phenylalanine, N-acyl tyrosine, their isomers, including their D and L isomers, salts, derivatives, and mixtures thereof. An example of a suitable N-acyl amino acid is N-undecylenoyl-L-phenylalanine is commercially available under the trail ENWHITE (Registered trademark) from Seppic (France).

Skin care agents and dermatologically acceptable carriers (see, e.g. [0316]-[0387]) are also disclosed in US Publication No. 2007/0020220A1, published Jan. 25, 2007, wherein the components/ingredients are incorporated herein by reference in their entirety.

The cosmetic composition may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide also refers to both naturally occurring and synthesized peptides. In one aspect, the peptides are di-, tri-, tetra-, penta-, and hexa-peptides, their salts, isomers, derivatives, and mixtures thereof. Examples of useful peptide derivatives include, but are not limited to, peptides derived from soy proteins, palmitoyl-lysine-threonine (pal-KT) and palmitoyl-lysine-threonine-threonine-lysine-serine (pal-KTTKS, available in a composition known as MATRIXYL®) palmitoyl-glycine-glutamine-proline-arginine (pal-GQPR, available in a composition known as RIGIN®), these three being available from Sederma, France, and Cu-histidine-glycine-glycine (Cu-HGG, also known as IAMIN®). In various aspects the cosmetic composition may comprise from about $1 \times 10^{-7}\%$ to about 20%, alternatively from about $1 \times 10^{-6}\%$ to about 10%, and alternatively from about $1 \times 10^{-5}\%$ to about 5% of the peptide.

In one aspect, the skin active agent is niacinamide. In one aspect, the agent is a combination of niacinamide, glycerine, tocopherol acetate, and D-panthenol. Niacinamide may be included in the composition in an amount between about 1% to about 30 wt %, in another aspect from about 2% to about 28 wt %, in another aspect from about 5% to about 25 wt %, and in another aspect from about 10% to about 20 wt %. When D-panthenol is included, it may be present in an amount of about 0.5% to about 5 wt %, or about 0.5% to about 3 wt % and/or about 0.5% to about 2 wt %. Glycerin may be included as an active in an amount from about 6% to about 20 wt %, and/or from about 8% to about 15 wt %, and/or from about 10% to about 15 wt %.

In various aspects, the skin active agent is selected from niacinamide, alone or in combination with one or more of palmitoyl-lysine-threonine, palmitoyl-lysine-threonine-threonine-lysine-serine, N-undecyl-10-enoyl-L-phenylalanine, retinyl propionate, N-acetyl glucosamine, vitamin C, tretinoin, salicylic acid, benzoic acid, benzoyl peroxide, tretinoin, and combinations thereof.

In an aspect the cosmetic compositions herein may be aqueous solutions, or emulsions as oil-in-water emulsions, water-in-oil emulsions or multiple emulsions having aqueous or oily external phases. In another aspect the cosmetic compositions herein are oil-in-water emulsions.

In one aspect to avoid a negative interaction with the pressure sensitive adhesive, the cosmetic composition comprises only low levels of silicones of about 0.5% to about 10%, and/or from about 1% to about 5% and/or the cosmetic composition is substantially free of silicones. As used herein "silicones" may refer to those silicones disclosed in US 2007/0020220A1, published Jan. 25, 2007, Osborne, for example in paragraphs [0226] to [0258].

In one aspect the cosmetic composition is substantially free of depilatory agents.

The cosmetic composition may comprise an effective amount of a skin active agent having activity to improve visual or aesthetic appearance of the skin, such as an agent effective to reduce or diminish the appearance of fine lines and/or wrinkles on human facial skin or an agent effective to treat existing acne lesions, reducing redness associated with acne lesions and/or protecting from formation of acne lesions.

In another aspect a method of treating skin is provided, comprising:
a. applying a cosmetic composition to a target area of the skin, comprising an effective amount of a skin active agent;
b. applying a multi-layered barrier patch to the target area of skin, wherein the barrier patch is adjusted to comprise:
  (i) a non-foamed first layer comprising a non-foamed polymer film having a first surface, having a thickness from 5 microns to 250 microns, preferably from 10 microns to 40 microns;
  (ii) a foamed second layer comprising a foamed polymer film comprising a Mean Void Volume Percentage from 45% to 80%, preferably from 50% to 75%, more preferably from 55% to 73%, and a thickness of from 10 microns to 250 microns, preferably from 40 microns to 160 microns;
wherein the cosmetic composition is at least partially in contact with the barrier patch.

The methods of treatment, application, regulation, or improvement disclosed herein may utilize the aforementioned products, compositions and/or multi-layered barrier patch. Application of the present compositions or multilayer barrier patch can occur on any target area of skin surface of the body. Skin surfaces of the most concern tend to be those not typically covered by clothing such as facial skin surfaces, hand and arm skin surfaces, foot and leg skin surfaces, and neck and chest skin surfaces (e.g., décolletage). In particular, application may be on a facial skin surface including the forehead, perioral, chin, periorbital, nose, and/or cheek skin surfaces.

The step of applying the cosmetic composition and/or barrier patch to a target area of skin may be done by localized application to the target area, for example an area that contains wrinkles. In reference to the application, the term "localized", "local", or "locally" mean that it is delivered to the target area of skin (such as an area of skin containing wrinkles) while minimizing delivery to skin surface not requiring treatment.

For aspects where the composition is applied separately from the barrier patch, the composition may be applied and lightly massaged into the skin. It is recognized that localized application does allow for a reasonable amount of the composition to be applied to areas adjacent to the wrinkles to be treated (i.e., the composition is unlikely to be applied or to remain within the boundary of the wrinkles without some spreading). The form of the composition or the dermatologically acceptable carrier should be selected to facilitate localized application.

Compositions and/or barrier patches of the present invention can be applied broadly to one or more facial skin surfaces to reduce the appearance of wrinkles within those facial skin regions.

The method of treating skin herein may optionally begin with a cleansing step. The consumer can wash his or her face with a suitable cleanser (e.g., Olay Purifying Mud Lathering Cleanser, available from The Procter & Gamble Company, Cincinnati, Ohio), and gently dry his or her skin.

The films disclosed herein may have a variety of applications but are of particular interest as films for beauty care products that may include products for the treatment of acne, diaper rash, application of deodorizing agents or cleaning agents to skin, and managing skin pH and other intimate wellness issues.

Test Methods

Flop Index

The FI is represented by the formula:

$$FI = 2.69 \times \frac{(L15 - L110)^{1.11}}{(L45)^{0.86}}.$$

L15 means 15 degree, L45 means 45 degree and L100 means 100 degree. The FI may be measured following ASTM E2539. A suitable measuring device includes a multi angle photometer MA98 from X-rite Company.

The standard sample is also the same as test sample outside. The standard test material is a white standard that is provided by X-Rite with the MA98 machine.

For multi-layered barrier patches that comprises no pigments, measure the FI on each side of the laminate and repeat each measurement three times on each side and take the average.

For multi-layered barrier patches that comprise pigments in the first layer or third layer but no pigment in the second foamed layer, measure the FI on the side of the barrier patch without pigments and repeat the measurement three times on that side and take the average.

The results of X-Rite MA98 include: L, a, b and FI. The various angles at which light reflection is measured in order to derive the values to put into the equation include: −15, 15, 25, 45, 75, 110. Since the difference between 15 degrees and 110 degrees gives a larger contrast, these are used for the Flop Index formula.

For all test methods, film samples are analyzed after first removing any consumer-removable release layer that may be present, such as a release layer protecting an adhesive layer or a gel layer.

Mean Void Volume Percentage Via MicroCT Analysis

For Mean Void Volume Percentage the thickness of any given layer of a film is determined by using scanning electron microscopy (SEM) to observe samples of the film prepared in transverse view (i.e., cross-section), in order to measure the thickness of each layer in micrometers.

The term "void" means a region which is devoid of solid film material composition, as determined by X-ray micro-computed tomography (microCT) imaging, using the method outlined below. For purposes of clarification, the void may have air, gases, moisture, and other non-solid components. MicroCT imaging reports the X-ray absorption of a sample in the three-dimensional (3D) Cartesian coordinates system. X-ray attenuation is largely a function of the material density of the sample, so denser materials require a higher energy to penetrate and appear brighter (higher attenuation), while void areas appear darker (lower attenuation). Intensity differences in grey levels are used to distinguish between void and non-void areas of the sample. Resolution is a function of the instrument characteristics and the operating settings used. The 3D dataset obtained of the sample is visualized, processed and analyzed via image processing software programs in order to measure 3D structures and intensities.

Test Method for Determining Foamed Layer Mean Void Volume Percentage

To determine the Mean Void Volume Percentage within a foamed layer[1], a sample of the undamaged film material is mounted inside a SCANCO Systems' model μ50 microCT scanner (Scanco Medical AG, Brüttisellen, Switzerland). The instrument's image acquisition settings are set according to the following specifications: an Energy level of 45 kVp; Intensity at 88 µA; 10 mm diameter tube; 1000 ms integration time; and 8 averaging. An isotropic spatial resolution of 1.8 µm voxels is required in the resulting microCT images of the sample. The 3D datasets are analyzed as 8-bit images (i.e., 256 grey levels).

[1]This method is applicable to the determination of the Mean Void Volume Percentage of foamed film layers and is not applicable to the Mean Void Volume Percentage of non-foamed film layers or non-foamed films.

Samples of test film material to be analyzed are prepared by punching sample discs out of the film using a sharp circular punch tool of approximately 8 mm diameter. These samples are laid flat and may be mounted between discs (and/or annuli) of a low-attenuating sample-preparation-foam, in alternating layers to form a stack. The use of mounting annuli can provide regions within the scans where each test sample is completely isolated from other solid material. The discs are mounted into a plastic cylindrical tube and secured inside the microCT scanner and scans are captured.

Software used for conducting the 3D reconstructions is the software that accompanies the scanner instrument, and is supplied by the instrument manufacturer (Scanco Medical AG, Brüttisellen, Switzerland). Software used for subsequent image processing steps and quantitative image analysis is the MATLAB program. A suitable version of the required software is MATLAB version 8.4.0.150421 (R2014b) with the following modules: Image Processing Toolbox version 9.1 (R2014b), Parallel Toolbox version 6.5 (R2014b), and Signal Processing Toolbox version 6.22 (R2014b) (The Mathworks Inc., Natick, Mass., U.S.A.), all run on operating system Windows 7 Professional Version 6.1 (build 7601: service pack 1) (Microsoft), along with Java Version 1.7.0_11-b21 (Oracle Corporation).

The 3D data set of each scanned test sample disc is trimmed to 1000×1000 voxels in the X-Y plane, and excludes any areas of the sample that contain noticeable tears or noise, and excludes the cut edge of the film sample. Each dataset is also trimmed in the Z direction such that the dataset volume comprises the full thickness of the sample disc as well as a volume of void air space above and below the thickness of the sample disc.

A preliminary grey level threshold value is determined independently for each trimmed 3D dataset. The preliminary threshold value is determined objectively by passing the dataset through the Graythresh Function in Matlab. This function determines a threshold value via the Otsu method, and is used to create a preliminary isolation of the film material voxels from the background and void voxels in the 3D dataset. Using the Matlab Connect-Components Function (bwconncomp), the largest Connected-Component is identified within each thresholded dataset in order to further eliminate stray noise outside the film.

From the data array comprising the largest Connected-Component, two-dimensional (2D) image slices are taken in both the X-Z direction and in the Y-Z direction (i.e., 1000 slices in each direction). In each of these 2D slices, Matlab is used to fit a Convex Hull Function around the full thickness of the film material in order to bridge across any apparent gaps in the outer layers of the film. Such apparent gaps in the outer layers may occur due to the relative size of the voxels versus the thickness of some thin layers, and additionally due to their relative alignment within the scan.

Void Volume Percentage values are derived only from the middle approximately 50% of thickness of the foamed layer being analyzed. The middle approximately 50% of thickness of the foamed layer is identified by observing the various structures in each slice, and a Mask overlay is created for each slice that represents and defines this area. The area of the mask is the middle approximately 50% of thickness of the foamed layer, is wholly contained within the foamed layer, and comprises only foamed layer composition and any voids contained therein. The region of all the mask slices is the same as the Region Of Interest (ROI) to be analyzed. Within the scanned dataset, the Matlab Convex Hull Function (regionprops with 'ConvexImage') defines the outer surfaces of the film, and as such the convex hull may be used as a reference location from which to create a mathematical label for the area of the mask. For example, in a specific sample slice an appropriate area for the mask might be observed to encompass the midpoint of the films' thickness and extends in the Z direction towards the upper convex hull surface as far as 25% of the total thickness and also extend toward the lower convex hull surface as far as 25% of the total thickness. One of skill will understand that different samples will likely require different locations for the masks, since the appropriate location is determined by the relative thicknesses and locations of the layers and structures present in each sample.

The 2D masks are combined to create a 3D mask. Two versions of the 3D mask are created, one version from each set of directional masks (i.e., X-Z and Y-Z). The original grey level intensity data within each mask volume comprises a 3D volume Region of Interest (ROI) within the middle area of the foamed layer. The Matlab Graythresh Function is used to analyze the grey level intensity data within the 3D mask ROI in order to determine a second, revised threshold. The revised threshold is applied to the data of the respective mask ROI to create the final separation of the film voxels from the background and void voxels.

A Void Volume Percentage value is calculated separately from each of the two mask ROIs. The calculation is conducted by dividing the number of non-void voxels (i.e. the number of voxels having an intensity grey level value greater than the revised threshold value), by the total number of voxels in the mask ROI, then subtracting this result from 1, then multiplying by 100, according to the following equation:

$$\text{Void Volume Percentage} = (1 - (\text{Non-Void Voxels in ROI}/\text{Total Voxels in ROI})) \times 100$$

The Mean Void Volume Percentage for each sample disc is calculated by averaging the void volume percentage values from the two mask ROIs in that dataset. Preferably, replicate sample discs are scanned and analyzed, and most preferably the replicate samples are obtained from different production batches of the film being tested. The values measured in all replicates are averaged to provide the reported Mean Void Volume Percentage of that foamed layer.

Surface Roughness (Ra)

The Surface Roughness (Ra) of the sample barrier patch or product is measured with the Surface Roughness Tester Surftest SJ-310 Series No. 178 available from Mitutoyo Corporation and according to the Surftest SI-310 Surface Roughness Tester Users Manual and Quick Reference Manual, No 99MBB463A1 Series No. 178 issued by Mitutoyo Corporation, Japan.

This instrument may be used to collect topographic data over a given area on a sample surface.

Sample Preparation: The film samples of the barrier patch or product for analysis are prepared by cutting a representative piece of the film/barrier patch approximately 2.5 centimeters by 4 centimeters and then a portion of the Sample was laid across a glass slide containing a double sided adhesive tape. The Sample is taped to eliminate or reduce wrinkling without stretching the film sample.

Measurement Conditions: A pre-calibration step is not used. Set the instrument to AUTO[2] as the setting for the measuring conditions prior to the Ra measurements. Measure the Ra for both sides of the Sample and in both the MD and the CD directions. Measure the Ra 4 times for each Sample.

[2] Page 6-28, Section 6.5.2 of the User Manual refers to the use of the Auto setting for Ra measurements.

WVTR

WVTR of the barrier patch is measured according to ASTM F1249 at 37° C. and 35% RH. Samples may be analyzed on a MOCON Permatran-W 3/33 Water Vapor Permeability Instrument using ASTM F1249. For samples with higher WVTR (e.g. from approximately 300 g/m$^2$/24 h to 500 g/m$^2$/24 h) samples may be analyzed per ASTM E-96 with desiccant placed inside the test cups and 35% RH surrounding the exterior of the cups. Samples of barrier patches are prepared and do not include the pressure sensitive adhesive.

Flexibility

The Kawabata KES-FB test is a Japanese quality judgment system for used for textile materials and is disclosed in "The Standardization and Analysis of Hand Evaluation (2nd Edition), Sueo Kawabata, July 1980, The Hand Evaluation and Standardization Committee, The Textile Machinery Society of Japan".

The Kawabata testing machine, KES-FB2-A. Pure Bend Tester for measuring Bending rigidity, B (gfcm$^2$/cm), may be used. For Bending Rigidity (B) with KES-FB2-A, measure the slope between 0.5 cm$^{-1}$ and 1.5 cm$^{-1}$ and −0.5 cm$^{-1}$ and −1.5 cm$^{-1}$. Perform the measurements in both directions (machine direction, MD, and cross direction, CD) with the following settings:

Total sample area: 20 cm×20 cm;
Maximum curvature: Kmax=±2.5 cm$^{-1}$;
Cycles=1;
Sensitivity=20;
Bending rate: 2.5 cm$^{-1}$/sec;
Bending deformation is applied to the width direction.
Prepare the samples as 20 cm×20 cm. 20 cm wide is the preferred sample width and the "Standard Condition" for the KES-FB2-A. If the samples are not 20 cm wide, cut them to the nearest whole number in centimeters and use the "Optional Condition" setting in the instrument which allows the width to be specified to the nearest centimeter. For example if the width is 17.5 cm, cut the sample to 17 cm wide, then specify the width as 17 cm. If samples are more flexible or less wide, then adjust sensitivity accordingly. Test sample n=2 replicates in the MD direction (bend in direction normal to the MD direction). Test sample n=2 replicates in the CD Direction.

Basis Weight

Basis Weight is calculated as follows. Sample Preparation: Samples were equilibrated at TAPPI conditions for 100 hours (50% RH, 23 C). Cut samples to 25.4 mm wide strips using JDC 1" strip cutter. Cut samples to 80 mm long using gage block. Weigh each sample using 4 place analytical balance. Basis weight is calculated as the sample mass/area, where mass is measured on the balance and area=25.4 mm×80 mm=2032 mm=0.002032 meters. Basis weight is reported in units of grams/meter$^2$.

Caliper/Thickness

Thickness measurement, other than thickness measurement for the calculation of Mean Void Volume Percentage, may be performed using ASTM D5729 which typically uses a pad caliper with a known pressure (0.1 psi) and a gage sensor. A Qualitest Thickness Tester, Model CHY-C2, available from www.WorldofTest.com may be used.

Opacity and Gloss

The test method for opacity is ISO method 6504. The thickness of film needs to be specified when opacity data is provided.

The test method for gloss is ASTM D2457 and a 60 degree angle is used.

EXAMPLES

The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein.

Example 1

Table 1 below provides the Mean Void Volume Percentages and other values of samples of multi-layered co-extruded films having varying degrees of foaming

TABLE 1

| Sample No. | Basis Weight (gsm) | No. of Layers Total Thickness | Mean Void Volume Percentage | FI | WVTR g/m2/ 24 hr | Flexibility gfcm$^2$/cm | Pearlescent Rating (1 to 10) | Opacity | Breathability Rating (1 to 10) | Gloss |
|---|---|---|---|---|---|---|---|---|---|---|
| 1-F767 (comparative) | 88 | 3 layer unfoamed film[3] ~81 μm | | 1.44 | 33.8 | 0.0204 0.0236 | 1 | 3.12% | 1 | 63.17% |
| 2-F738 | 99 | 3 layer film[4] core layer foamed ~182 μm | 60.34% | 4.04 | | 0.0416 0.0434 | 9 | 43.63% | 7 | 18.13% |

TABLE 1-continued

| Sample No. | Basis Weight (gsm) | No. of Layers Total Thickness | Mean Void Volume Percentage | FI | WVTR g/m2/ 24 hr | Flexibility gfcm²/cm | Pearlescent Rating (1 to 10) | Opacity | Breathability Rating (1 to 10) | Gloss |
|---|---|---|---|---|---|---|---|---|---|---|
| 3-F584 | 99 | 3 layer film[5] Core layer foamed ~170 μm | 63.27% | 4.35 | 82 | 0.0475 0.0295 | 9 | 32.39% | 7 | 16.67% |
| 4-F769 | 86 | 2 layer[6] one foamed layer ~177 μm | 65.57% | 3.12 (foamed side) 4.83 (non foamed side) | | 0.042 0.031 | 5 7 | 42.42% 39.08% | 7 | 7% (foamed) 24.67% |
| 5-F777 | 68 | 3 layer[7] core foamed ~163 μm | 73.82% | 3.59 | | 0.0245 0.012 | 7 | 41% | 9 | 15.53% |
| 6-F778 | 105 | 3 layer[8] foamed core and non foamed first and third layers ~162 μm | 55.75% | 3.89 | | 0.0555 0.0615 | 7 | 32.94% | 5 | 19.43% |

[3]All layers made of EVA; the dimensions programmed into the film equipment were intended to provide outside layers each having 20 μm thickness and core foamed layer having 60 μm thickness.
[4]All layers made of EVA; the dimensions programmed into the film equipment were intended to provide outside layers each having 20 μm thickness and core foamed layer having 130 μm thickness.
[5]All layers made of EVA; the dimensions programmed into the film equipment were intended to provide outside layers each having 20 μm thickness and core foamed layer having 130 μm thickness.
[6]All layers made of EVA; the dimensions programmed into the film equipment were intended to provide outside layer having 40 μm thickness and core foamed layer having 130 μm thickness.
[7]All layers made of EVA; the dimensions programmed into the film equipment were intended to provide outside layers each having 20 μm thickness and core foamed layer having 130 μm thickness.
(Score of 1 = least pearlescent or appearance of breathability and Score of 10 = most pearlescent or higher appearance of breathability)

TABLE 2

| Film Material | FI | Gloss (at 60 degree) | Ra Side A Length | Ra Side A Width | Ra Side B Length | Ra Side B Width |
|---|---|---|---|---|---|---|
| 0% Foaming PE | | Side A-0.282 A-75.94 Side B-0.436 B-66.2 | 1.883 | 0.863 | 1.475 | 0.778 |
| 20% Foaming PE[9] | | Side A-0.338 A-69.84 Side B-2.258 B-74.1 | 1.779 | 1.99 | 1.416 | 1.889 |
| 40% Foaming PE | | Side A-0.228 A-72 Side B-2.444 B-75.4 | 2.072 | 2.553 | 1.591 | 2.206 |
| F626[10] | | Side 1-12.90 Side 1-8.7 Side 2-14.97 Side 2-13.57 | | | | |
| F769[11] | 4.034 | 17.2 (both sides substantially same) | 18.537 | 19.097 | 26.526 | 27.081 |
| F149[12], 80GSM | 3.7; 3.94 | 17.2; 15.5 | 19.999 | 18.354 | 20.305 | 18.747 |
| F149b[13] 100GSM | 3.908; 3.992 | 21.78; 13.66 | 14.312 | 13.874 | 14.102 | 15.753 |
| F767[14] | 1.552 | 42 (both sides substantially same) | 0.796 | 1.044 | 0.626 | 0.949 |
| F584[15] | 4.166 | 16.06 (both side substantially same) | 15.96 | 16.567 | 15.334 | 14.358 |

[8]All layers made of EVA; outside layers each had 20 μm thickness and core foamed layer had 130 μm thickness.
[9]Substantially free of pigments.
[10]Three layer film having a Basis Weight of 201gsm, wherein each layer comprises EVA. The thickness is approximately 368.1 μm.
[11]See also Table 1.
[12]Three layer film having a Basis Weight of 80 gsm, wherein each layer comprises EVA.
[13]Three layer film having a Basis Weight of 100 gsm, wherein each layer comprises EVA.
[14]See also Table 1.
[15]See also Table 1.

The samples (1, 2, 3, 4, 5 and 6) of Table 1 are either 2 layer or 3 layer film laminates. Some samples have a first layer of a non-foamed EVA, a foamed second layer of EVA, and in some samples, third layer of a non-foamed EVA. The foamed EVA second layer is in-between the first and third non-foamed layers. The Mean Void Volume Percentage is determined as described herein.

Sample 1 contains no foamed layer and is therefore a comparative example. A small-base of consumers evaluated the barrier patches of Samples 1-6 shown above in Table 1. The barrier patches varied in flexibility, FI, WVTR, basis weight, Void Volume Percentage, etc. as shown in Table 1.

Sample 2 had the highest ratings by consumers for the Ratings tested, though Sample 5 was also highly rated and consumers rated that it looked more breathable than Sample 2. Consumers rated Sample 5 however, as being more flexible than Sample 2.

The foamed film Sample 2 is stiffer than unfoamed film Sample 1, even though these have similar basis weights. This is because Sample 2 is thicker than Sample 1 due to foaming and since stiffness of a film is related to the thickness. The fact that Sample 2 is stiffer makes it less likely to wrinkle on the face than Sample 1, but does so without making the film heavier, e.g. the basis weights of Samples 1 and 2 are similar. To increase the stiffness of an unfoamed film, one would have to increase the thickness which would considerably increase its basis weight. Thus this film would feel heavier.

Sample 4 was a 2 layer film wherein the foamed side layer (foamed second layer) has a different appearance than the unfoamed layer or skin layer (non-foamed first layer). Consumer determined that the foamed side looks soft with less gloss which appeared to be breathable.

Sample 5 has the highest level of foaming of the Samples. This sample had a higher Void Volume Percentage value and scored well on the Breathability Rating. However, this film is more flexible versus Sample 2 even though it had similar thickness as Sample 2. Sample 5's Flexibility value is higher than that of the Sample 2 which may be due to the lower basis weight which also has some influence on film stiffness.

Sample 6 has the lowest level of foaming of the 6 Samples (except for the comparative sample). It has the highest Kawabata Flexibility bending stiffness of the foamed films possibly in part due to having the least degree of cavitation from foaming and hence it has a higher basis weight.

Table 2 shows Surface Roughness (Ra) values for the barrier patch or product disclosed herein.

Figure 4:
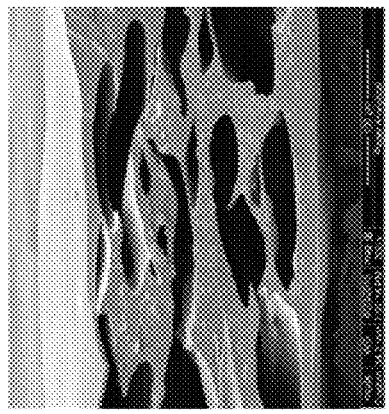
FIG. 4 is an SEM cross section image, in the machine direction, of a barrier patch without foaming.
Figure 5:
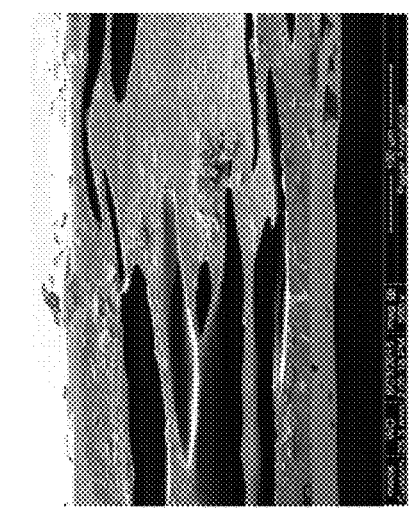
FIG. 5 is an SEM cross section image, in the machine direction, of a barrier patch with foaming.
Figure 6:
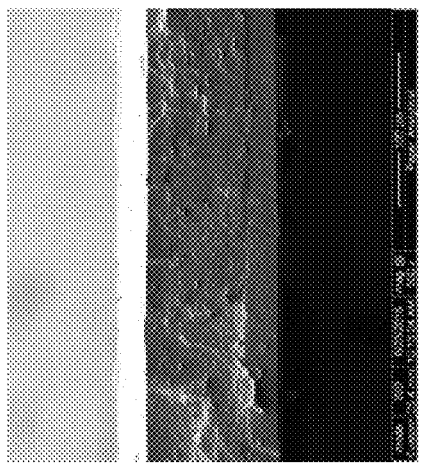
FIG. 6 is an SEM cross section image, in the machine direction, of a barrier patch with foaming.

FIGS. 4, 5 and 6 show 3 SEM images of cross sections (in the machine direction) of 3 barrier patches. FIG. 4 shows Sample 1 (F767), an unfoamed film.

FIG. 5 is a cross section SEM image of Sample 5 (F777) which has a higher degree of foaming and having a Mean Void Volume Percentage of 73.82%. FIG. 5 shows a three layer barrier patch comprising a non-foamed first layer, a foamed second layer, and a non-foamed third layer.

FIG. 6 shows an SEM image of Sample 6 (F778) with a lower degree of foaming Sample 6 (F778) comprises a three-layer co-extruded barrier patch having non-foamed first layer, a foamed second layer and a non-foamed third layer. Sample 6 has a Mean Void Volume Percentage of 55.76%

Figure 7:
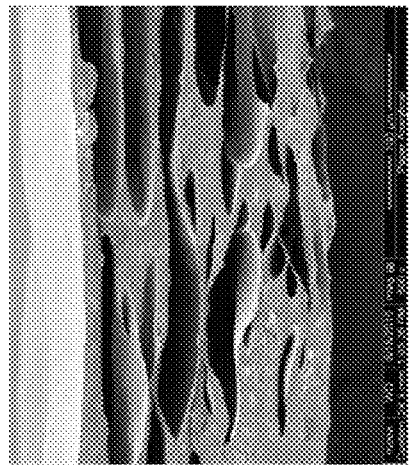
FIG. 7 is an SEM image showing a top view of a foamed layer of a barrier patch.
Figure 8:
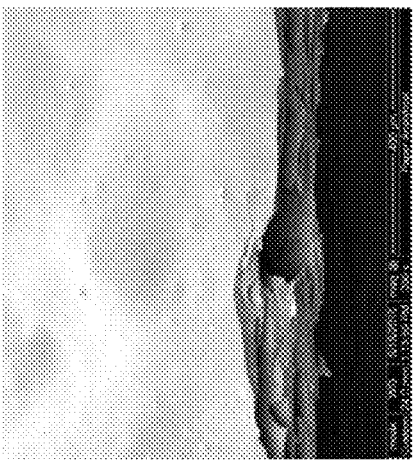
FIG. 8 is an SEM image showing a top view of an unfoamed layer of a barrier patch.
Figure 9:
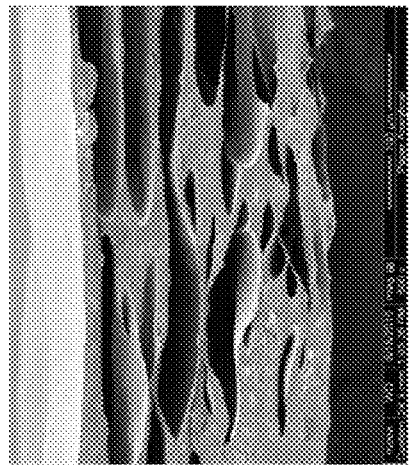
FIG. 9 is an SEM cross section image, in the machine direction, of a barrier patch with foaming.

FIGS. 7, 8 and 9 show 3 SEM images of Sample 4 (F769). FIG. 7 shows a top view with the foamed side up. FIG. 8 shows a top view of Sample 4 with the first layer non-foamed side up, and FIG. 9 shows a cross section view of the multilayer barrier patch in the machine direction.

Exemplary products, for example Products A, B, C or D, for treatment of periorbital skin aging are attached, via the adhesive side, to periorbital area. The Product is applied and worn for an extended period of time of approximately 7-8 hours and thereafter removed. The Products herein deliver an effective amount of the skin active agent in a manner that achieves penetration of the skin active agent into the stratum corneum, and/or other layers of the epidermis, and in many aspects, into the basal skin layer and/or dermis.

Example 2

A representative barrier patch may be made via the following process. An EVA polymer (for example Dupont Elvax® Grades: 260, Grade 250, Grade 150, 150 W, and/or Grade 40 W), is fed into an extruder wherein 100 percent $CO_2$ or nitrogen is metered into the extrusion barrel as a blowing agent to provide physical foaming. The EVA polymer is blended with polyethylene at a ratio of 80% EVA and 20% PE. Other blends may be use including 75% EVA and 25% PE, 70% EVA and 30% PE, and 65% EVA and 35% PE or the PE used is from about 20% to about 40% by wt of the blend. Additives, such as slip agents, antistatic agents or fillers, etc. may also be used in the blend. The end of the extruder is also equipped with static mixers to improve the mixing of the polymer/blowing agent mixture. Simultaneously, a 1.00% blend of the EVA resin is fed into another extruder without blowing agent, for production of the co-extruded unfoamed solid skin layers. The barrier patch may comprise one or more non-foamed skin layers, preferably 2 skin layers. The EVA/PE resin blend is foamed and coextruded with non-foamed EVA (without PE) to form a sheet/laminate having a foamed core resin with two solid skin layers adhered to both sides of the core resin layer.

Prior to foaming the layer distribution may be approximately 20-30 µm unfoamed skin layers, with a 60 µm foamed layer. Foaming of the core layer potentially boosts the core layer caliper from 60 µm to a range of 120 µm to 140 µm. A pressure sensitive adhesive layer may then be coated on the barrier layer such as via a process known in the art. A cosmetic composition, such as one of those disclosed below in the Examples, may then be coated on the pressure sensitive adhesive via a process known in the art, and then any solvents, if present, may be removed via drying.

Example 3: Cosmetic Compositions

| Example | 1 | 2 | 3 | 4 | 5 |
|---|---|---|---|---|---|
| Phase A | | | | | |
| Distilled water | qs 100 | qs 100 | qs 100 | qs 100 | qs 100 |
| Phase B | | | | | |
| Glycerin | 5 | 5 | 5 | 6 | 6 |
| Ti02 | 0.75 | 0.75 | 0.75 | 0.75 | 0.75 |
| Phase C | | | | | |
| Glycerin | 1 | 1 | 1 | 3 | 3 |
| EDTA | 0.1 | 0.1 | 0.1 | 0.1 | 0.1 |
| Carbopol 954 | 0.68 | 0.5 | 0.5 | 0.4 | 0.4 |
| Carbopol 1382 | 0.1 | 0.1 | 0.1 | | |
| Phase D | | | | | |
| Cetyl Palmitate | | | | 1.5 | 1.5 |
| Cetyl Alcohol | 0.72 | 0.72 | 0.72 | 2.25 | 2.25 |
| Stearyl Alcohol | 0.48 | 0.48 | 0.48 | 1.5 | 1.5 |
| Stearic Acid | 0.1 | 0.1 | 0.1 | 0.31 | 0.31 |

-continued

| Example | 1 | 2 | 3 | 4 | 5 |
|---|---|---|---|---|---|
| PEG-100 Stearate | 0.1 | 0.1 | 0.1 | 0.31 | 0.31 |
| Silicone Wax DC2501 | | | | 2 | 2 |
| DC 3225C | | | | 1.88 | 1.88 |
| Dimethicone 200/350 cst | | | | 0.63 | 0.63 |
| Arlatone 2121 | 1 | 1 | 1 | | |
| Silicone Q21403 | 2 | 2 | 2 | | |
| Fatty acid ester of sugar | 0.67 | 0.67 | 0.67 | | |
| Tocopherol Acetate | | | 0.5 | | 0.5 |
| Niacinamide | 2 | 2 | 2 | 2 | 2 |
| Phase E | | | | | |
| Distilled water | 2 | 2 | 2 | 2 | 2 |
| NaOH to neutralize Carbopols | to neutralize | to neutralize | to neutralize | to neutralize | to neutralize |
| Phase F | | | | | |
| Urea | 2 | | | | |
| D-Panthenol | | | 0.5 | | 0.5 |
| Distilled water | 5 | 5 | 5 | | 5 |
| Phase G | | | | | |
| Glydant Plus | 0.1 | 0.1 | 0.1 | 0.1 | 0.1 |
| Glycerin | 1 | 1 | 1 | 1 | 1 |
| Distilled water | 1 | 1 | 1 | 1 | 1 |
| Phase H | | | | | |
| Methyl Isostearate | 1.33 | | | | |
| Isopropyl Isostearate | | 1.33 | 1.33 | | |
| Isopropyl Palmitate | | | | 1.25 | 1.25 |
| Retinol | | | | 0.04 | 0.04 |
| BHT | | | | 0.05 | 0.05 |
| Tween 20 | | | | 0.04 | |
| Tween 80 | | | | | 0.04 |

Oil-in-water emulsions are prepared from the ingredients in these examples using conventional formulating techniques. First, sparge Phase A ingredients using nitrogen for approximately 15 minutes. Phase B ingredients are milled until the Ti02 is homogeneously dispersed, and then added to Phase A. Phase C ingredients are then dispersed into Phase A/B until uniform using propeller type mixing and heating the mixture to about 75° C. In a separate vessel, Phase D ingredients are combined and heated to about 75° C. The mixture of phases A/B/C are then blanketed with a slow, steady stream of nitrogen. Next the Phase D ingredients are homogenized into the mixture of phases A/B/C using any rotor/stator type of homogenizer for approximately 15 minutes. After 15 minutes, the mixing is switched to low rpm sweep mixing. Next, phase E ingredients are combined and added to the mixture of phases A-D.

Once phase E is mixed and the batch mixture is homogeneous, the entire batch mixture is cooled. When the batch is cooled to about 50° C., phase F ingredients are added and homogenized. When the batch is cooled to about 40° C., phase G ingredients are added to the batch mixture. Lastly, when the batch mixture is cooled to about 30° C., the phase H ingredients are combined to the batch mixture. Mixing is continued until the batch mixture is uniform.

Delivery of Skin Active Agent to a Target Area of Skin.

The above cosmetic compositions may be applied via the fingertips to the periorbital area of the face of a human test subject to provide from about 0.5 mg/cm2 to about 3 mg/cm2 of the cosmetic composition to the target area of skin. Thereafter an exemplary orbital barrier patch, for example Samples 2, 4, 5 and 6 of Example 1, for treatment of periorbital skin aging is attached to periorbital area, covering the cosmetic composition. The barrier patch of the invention may be applied and worn for an extended period of time of approximately 7-8 hours and thereafter removed.

The products and methods herein deliver an effective amount of the skin active agent in a manner that achieves penetration of the skin active agent into the stratum corneum, and/or other layers of the epidermis, and in many aspects, into the basal skin layer and/or dermis.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A beauty care product comprising:
    a multi-layered barrier patch comprising:
        (i) a non-foamed first layer comprising a non-foamed polymer film having a first surface, having a thickness from about 5 microns to about 250 microns;
        (ii) a foamed second layer comprising a foamed polymer film comprising a Mean Void Volume Percentage from about 45% to about 80%, and a thickness of from about 10 microns to about 250 microns;
        wherein the foamed second layer comprises from about 15% to about 40%, of polyethylene (PE) and from about 60% to about 85%, of ethylene vinyl acetate (EVA);
    a cosmetic composition comprising an effective amount of a skin active agent; and
    a pressure sensitive adhesive.

2. The product of claim 1 wherein the Mean Void Volume Percentage is from about 50% to about 75%.

3. The product of claim 1 wherein the barrier patch further comprises a WVTR from about 1 g/m²/24 h to about 500 g/m²/24 h.

4. The product of claim 3 wherein the barrier patch comprises a WVTR from about 1 g/m²/24 h to about 250 g/m²/24 h.

5. The product of claim 1 wherein the barrier patch is water impermeable.

6. The product of claim 1 wherein the barrier patch further comprises a Surface Roughness (Ra) from about 3 to about 30.

7. The product of claim 6 wherein the Surface Roughness is from about 4 to about 29.

8. The product of claim 1 wherein the barrier patch is substantially free of pigments.

9. The product of claim 1 wherein the multi-layered barrier patch further comprises a non-foamed third layer having a thickness from about 5 microns to about 250 microns, wherein the foamed second layer is in between the non-foamed first layer and the non-foamed third layer.

10. The product of claim 1 wherein the barrier patch further comprises a first surface and the pressure sensitive adhesive is in contact with at least part of the first surface of the barrier patch.

11. The product of claim 1 wherein the pressure sensitive adhesive is selected from the group consisting of acrylic and methacrylic ester homo- or copolymers, butyl rubber based systems, silicones, urethanes, vinyl esters and amides, olefin copolymer materials, styrene/isoprene diblock copolymers; styrene/butadiene diblock copolymers; butylene/ethylene/styrene triblock copolymers, and combinations thereof.

12. The product of claim 1 wherein the composition comprises from about 0.01% to about 10% of a skin active agent selected from the group consisting of vitamin E, vitamin A, vitamin B, niacinamide, glycerine, tocopherol acetate, D-panthenol, palmitoyl-lysine-threonine, palmitoyl-lysine-threonine-threonine-lysine-serine, N-undecyl-10-enoyl-L-phenylalanine, retinyl propionate, N-acetyl glucosamine, vitamin C, tretinoin, salicylic acid, benzoic acid, benzoyl peroxide, tretinoin, and combinations thereof.

13. The product of claim 1 wherein the barrier patch has a total thickness of about 20 microns to about 500 microns.

14. The product of claim 1 wherein the cosmetic composition is an oil in water emulsion.

15. The product of claim 1 wherein the barrier patch is substantially free of a non-woven material.

16. A beauty care product comprising:
a multi-layered barrier patch comprising:
(i) a non-foamed first layer comprising a non-foamed polymer film having a first surface, and having a thickness from about 5 microns to about 250 micron; wherein the non-foamed first layer is substantially free of pigments;
(ii) a foamed second layer comprising a foamed polymer film comprising ethylene vinyl acetate, having a Mean Void Volume Percentage from about 45% to about 80% and a thickness of from about 10 microns to about 250 microns;
wherein the barrier patch comprises a Surface Roughness from about 3 to about 30;
wherein the foamed second layer comprises from about 15% to about 40%, of polyethylene (PE) and from about 60% to about 85%, of ethylene vinyl acetate (EVA);
a cosmetic composition comprising an effective amount of a skin active agent; and
a pressure sensitive adhesive.

17. The product of claim 16 wherein the ethylene vinyl acetate polymer has an ethylene-to-vinyl acetate monomer ratio of about 4:1 to about 1:1.

18. The product of claim 16 wherein the ratio is from about 3:1 to about 3:2.

19. The product of claim 16 wherein the barrier patch further comprises a WVTR from about 1 $g/m^2/24$ h to about 500 $g/m^2/24$ h.

20. The product of claim 16 wherein the barrier patch is water impermeable.

21. The product of claim 16 wherein the barrier patch further comprises a Flop Index (FI) from about 2.5 to about 15.

22. The product of claim 16 wherein the barrier patch is substantially free of pigments.

23. The product of claim 16 wherein the barrier patch further comprises a flexibility from about 0.009 $gfcm^2/cm$ to about 0.14 $gfcm^2/cm$.

24. The product of claim 16 wherein the non-foamed first layer comprises a non-foamed polymer film comprising ethylene vinyl acetate.

25. The product of claim 24 wherein the multi-layered barrier patch further comprises a non-foamed third layer having a thickness from 5 microns to 250 microns and wherein the foamed second layer is in between the non-foamed first layer and the non-foamed third layer.

26. The product of claim 16 wherein the barrier patch is substantially free of a non-woven material.

27. The product of claim 16 wherein the Mean Void Volume Percentage is from about 50% to about 75%.

28. The product of claim 21 wherein the barrier patch further comprises a Flop Index (FI) from about 3 to about 6.

* * * * *